United States Patent [19]

Homburg

[11] 4,228,636
[45] Oct. 21, 1980

[54] METHOD AND APPARATUS FOR THE MEASUREMENT OF PLANT DENSITY FOR THE CONTROL OF HARVEST MACHINES

[75] Inventor: Helmut Homburg, Harsewinkel, Fed. Rep. of Germany

[73] Assignee: Firma Gebr. Class Maschinenfabrik GmbH, Fed. Rep. of Germany

[21] Appl. No.: 11,592

[22] Filed: Feb. 12, 1979

Related U.S. Application Data

[63] Continuation-in-part of Ser. No. 770,126, Feb. 18, 1977, abandoned.

[30] Foreign Application Priority Data

Feb. 27, 1976 [DE] Fed. Rep. of Germany ....... 2608049

[51] Int. Cl.³ .................. A01D 45/00; A01D 75/02
[52] U.S. Cl. .................. 56/10.2; 56/DIG. 15
[58] Field of Search ............ 56/10.2, DIG. 15, 312

[56] References Cited

U.S. PATENT DOCUMENTS

| | | | |
|---|---|---|---|
| 2,746,230 | 5/1956 | Reimer | 56/312 |
| 3,094,693 | 6/1963 | Taylor | 56/DIG. 15 |
| 3,563,013 | 2/1971 | Elfes | 56/10.2 |
| 3,583,514 | 6/1971 | Taylor | 56/10.2 |
| 3,593,720 | 7/1971 | Botterill et al. | 56/DIG. 15 |
| 3,606,742 | 9/1971 | Wieneke | 56/10.2 |
| 3,797,208 | 3/1974 | Strubbe | 56/10.2 |
| 3,935,866 | 2/1976 | Northrup | 56/DIG. 15 |
| 3,939,846 | 2/1976 | Drozhzhin et al. | 56/DIG. 15 |
| 3,972,381 | 8/1976 | Gail | 56/10.2 |

FOREIGN PATENT DOCUMENTS

| | | | |
|---|---|---|---|
| 2451314 | 5/1976 | Fed. Rep. of Germany | 56/10.2 |
| 69234 | 10/1969 | German Democratic Rep. | 56/DIG. 15 |

*Primary Examiner*—Paul J. Hirsch
*Attorney, Agent, or Firm*—Pollock, Vande Sande & Priddy

[57] ABSTRACT

The density of plant growth in front of a harvester machine is measured, to control the operating rate of the machine, by producing an ultrasonic field immediately forward of the cutters on the machine, which field comprises at least one ultrasonic beam of frequency modulated ultrasonic impulses. The apparatus employed comprises two transducers consisting respectively of an ultrasonic transmitter and an ultrasonic receiver respectively located on opposite sides of the machine immediately forward of the cutting blades and oriented on a line therebetween disposed orthogonally to the direction of travel of the machine, and at least one further ultrasonic transducer disposed adjacent one of said two transducers but oriented on a line relative to the other of said two transducers which line is inclined relative to the direction of travel of the machine.

9 Claims, 3 Drawing Figures

METHOD AND APPARATUS FOR THE MEASUREMENT OF PLANT DENSITY FOR THE CONTROL OF HARVEST MACHINES

CROSS REFERENCE TO RELATED APPLICATION

This application is a continuation-in-part of prior copending application, Ser. No. 770,126, filed Feb. 18, 1977 now abandoned.

BACKGROUND OF THE INVENTION

The present invention relates to a method of measuring the density of standing plants, in order to control the rate of operation of harvest machines, by use of an ultrasonic field which permeates the uncut growth immediately forward of the cutters, the drop in intensity of which between the untrasonic transmitter and receiver is converted into a control signal. The invention relates furthermore to apparatus on a harvest machine such as a combined harvester for controlling the machine's operating rate by measurement of the density of growth using an ultrasonic field immediately forward of the harvest tools such as cutting knives in the direction of travel, said apparatus including an ultrasonic transmitter and an ultrasonic receiver arranged at right angles to that direction on opposite sides of the machine.

It is known, when measuring the density of grain crop growth, to set cut plants in a strip of predetermined width and to subject this as a medium of irregular distribution in a homogeneous medium air to an ultrasonic field, the effect upon which is used as a measure of the average distribution. It is also known to increase the width of the sounded strip to that of the operating width of the machine, making it possible to obtain automatically the growth density and density changes in front of the harvest machine cutters, so that the rate of the harvest machine can be controlled in dependence upon the measured plant density value. For this purpose, a method has already been developed for ultrasonically measuring the growth density or changes in the growth density sufficiently in advance of the harvester cutters, without alteration to the plants. To do this, the necessary ultrasonic transmitter and receiver are arranged on a suitable carrier in the immediate vicinity of the cutters so that the data obtained can be evaluated and used at once to control, for instance, the forward rate of travel of the harvester.

It has already been realized that suitable values for measuring the density of plant growth by means of ultrasonic fields on harvest machines can only be provided when interference noise, especially that made by the harvest machine itself, is suppressed. For this reason, filter means have been introduced into the electroacoustic transformer to hold back the interference frequencies.

The precautions taken in the past, however, have been insufficient because the frequency spectrum of interference noise produced by the multi-blade cutters extends high into the ultrasonic zone, frequently causing incorrect measurements on the known types of ultrasonic measuring devices for harvest machines. With the known methods and devices, the intensity of the ultrasonic vibrations is tested only after passing through the strip being measured, and the amplitude of the acoustic pressure is used to form the control signal. The heterodyne interference in the ultrasonic field of measurement can lead to considerable distortion of the amplitude, whereby even an increase in the amplitude is possible although a decrease in the intensity of the ultrasonic vibrations would normally be expected due to absorption and reflection over a large distance.

Furthermore, the strip being ultrasonically measured can only be a short distance in front of the cutting means and thus in a zone in which the level of interference is unavoidably high. Apart from this, the absorption alone is not proportional to the density of plant growth because of weeds, undergrowth, and bald or dense patches. In all, on large harvest machines, the signal reaching the receiver is so weak and distorted that on the one hand it is dependent on the contingencies in the vicinity of the receiver, and on the other hand, even the normal differences in growth across the cutting width have little in common with the true average value.

It is therefore the purpose of the present invention, while avoiding the above-mentioned disadvantages, to provide a control signal which is sufficiently proportional to the growth density across the entire width of the cutters on a large harvest machine, and which is independent of interference at ultrasonic frequencies produced by the cutting means in the harvester.

BRIEF SUMMARY OF THE INVENTION

According to the invention, this purpose is achieved for a method as initially described above, in that the ultrasonic field created takes the form of at least one intermittent ultrasonic beam of frequency modulated ultrasonic impulses, the time lapse and/or phase displacement of which between the transmitter and receiver is evaluated for use as a control signal.

The special advantage of the method according to the invention is that apart from the intensity, the time lapse of the ultrasonic impulses is also measured, which of course presupposes impulse generation at the transmitter. By means of the predetermined impulse intervals, the irregular interference impulses at the receiver can be eliminated. The periodical or unperiodical frequency modulation of the ultrasonic impulses aids in avoiding disadvantages of interference phenomena. This is important for the vertical sounding over the shortest distance between transmitter and receiver in order to compensate the interference maxima and minima. This ensures that the output signal reaches the receiver with maximum intensity. Finally, measuring the phase rotation within the individual impulses has the advantage that the divergence of the individual impulses can be registered in order to increase the forward limits of the ultrasonic measurement. Thus, not only the density of growth immediately between the transmitter and receiver can be registered, but also that which lies in front of the harvester in the direction of movement thereof, now made measurable because of the impulses delayed by reflection.

In a further advantageous development of the invention, the ultrasonic impulses can be combined with interference noise taken from the zone of measurement, which interference is then eliminated by comparing the difference between the transmitted and the received ultrasonic impulses. More particularly, the interference noise is registered by means of an additional microphone and electro-acoustically transformed to an interference signal which can then be subtracted from the signal produced by the ultrasonic impulse receiver, thus substantially removing the disturbance.

Furthermore, it can also be advantageous to make use of selective, electro-acoustic transducers capable of functioning both as transmitters and as receivers which continuously reverse the direction of the ultrasonic impulses. The transmitter and receiver functions of the transducers are periodically or non-periodically reversed, whereby the averaging effect over the entire width of the measured growth is further improved.

It is of further advantage if the echo of the transmitted ultrasonic impulses is registered on the same side as the transmitter, and then used in the evaluation of the receiver signal. A measure for the density of plant growth is provided by the ultrasonic vibrations reflected back to the transmitter, whereby in extreme cases of great plant growth density, it can occur that the impulses arriving at the receiver are too weak to be evaluated, but the echoed impulses offer a much less distorted result.

By means of further additional receivers such as microphones, the reflection can be registered to further advantage out of the depths of the plant growth. Suitably, for this purpose, microphones with a corresponding directional effect are used which are situated at positions other than those of the ultrasonic receiver or transmitter. The deflected ultrasonic impulses are registered which are reflected through the plant growth to the same side as the transmitter or to the same side as the receiver or to a plane arranged on an incline thereto. Depending upon whether the reflected impulses are received on the same side as the receiver or the transmitter, subtraction from or addition to the other impulses picked up at the receiver results in a signal which is substantially equivalent to the average plant growth density.

Finally, for the utilization of the method according to the invention, it can be advantageous for bridging greater distances of ultrasonic measurement to operate the ultrasonic transmitter and receiver on two different frequencies together. Thus, at least two ultrasonic impulses with instantly discernible frequencies are simultaneously transmitted and reach the transmitter correspondingly at variance, whereby the control signal can be formed from one of these impulses or from a combination of both.

For the above-described method, use is preferably made of an arrangement which is principally suited to combined harvesters, wherein an ultrasonic transmitter and an ultrasonic receiver are situated immediately forward of the harvesting tools such as cutting blades, on opposite sides in a line transverse to the direction of travel of the harvester, and wherein said arrangement includes, besides the ultrasonic transmitter and/or besides the ultrasonic receiver, at least one additional transmitter or receiver arranged on a line to the opposite transmitter which line is inclined relative to the direction of movement of the harvester.

This arrangement advantageously permits the transmission of ultrasonic impulses from different positions to a single receiver or vice versa, and also makes it possible to work with several ultrasonic beams simultaneously.

BRIEF DESCRIPTION OF THE DRAWINGS

The apparatus proposed by the invention is explained below in detail by the use of a preferred embodiment and with reference to the drawings, where.

DETAILED DESCRIPTION OF PREFERRED EMBODIMENTS

Figure 1:
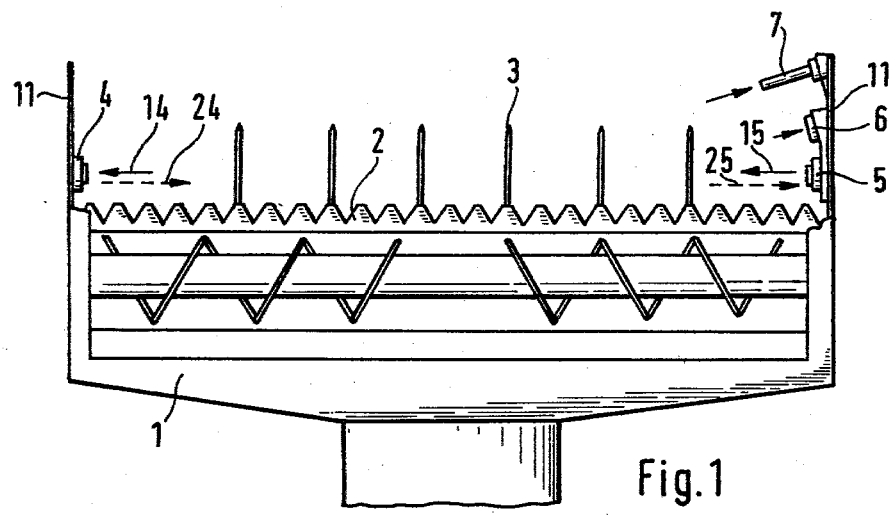
FIG. 1 shows a top view of the cutting unit of a reaping and threshing machine with an ultrasonic measuring unit attached thereto.

FIG. 1 depicts a cutter through 1 of a reaping and threshing machine that is joined in front by a reaping bar 2. Over the reaping bar 2 there protrudes in a forward direction stalk lifters 3 that tilt from the lower front to the upper rear. Cutting jaws 11 are positioned laterally of the cutter trough 1 and parallel to the stalk lifters 3. The cutting jaws 11 line the sides of the entire cutting and collecting system of the reaping and threshing machine. At one of the cutting jaws 11 there is mounted an ultrasonic transmitter 4. An ultrasonic receiver 5 is mounted on the other of the cutting jaws 11 opposite the transmitter 4. It should be appreciated that the illustrated positions of the transmitter 4 and receiver 5 are not critical, since the transmitter may operate as a receiver and the receiver may operate as a transmitter.

Between the ultrasonic transmitter 4 and the ultrasonic receiver 5 there is present an ultrasonic field which is formed by ultrasonic pulses. The ultrasonic field extends in front of the reaping bar 2, viewed in the direction of feed, so that the material to be harvested will be covered by the ultrasonic field during the cutting operation. Subject to the density of the stalks of the material to be harvested, the ultrasonic pulses will search for a path from the transmitter 4 to the receiver 5 which will not always correspond to the shortest distance. Due to reflection, one portion of the ultrasonic pulses will travel this path by way of a longer route, and one portion of the pulses will be absorbed in the course of their travel or reflected in the opposite direction.

In the embodiment illustrated, the transmitter 4 emits a beam 24 comprised of ultrasonic pulses. The pulses arrive at the receiver 5 in the form of a beam 25. The receiver 5 emits at the same time a beam 15 which consists also of ultrasonic pulses and which is received at the transmitter 4 in the form of a beam 14.

A substantial portion of the two beams 24 and 25 is attenuated by reflection or absorption. Thus, a reflection receiver 6 and a directional microphone 7 are positioned at the jaw 11 on the receiver side of the apparatus of FIG. 1 to allow a more complete acquisition of information from the pulses. A line taken between either the reflection receiver 6 or the directional microphone 7 and the transmitter 4 is inclined relative to the direction of feed, and thus is also inclined relative to the transverse direction of the cutting tool, so that the density of the vegetation is measured not only in a straight line but also across a fanshaped area. Thus, the directional microphone 7 acquires its ultrasonic pulses, so to speak, from the depths of the vegetation by receiving the deflected portions of the ultrasonic pulses that are emitted by the transmitter 4 and reflected away from the direction of the beams 24 and 25. The reflection receiver 6 on the other hand receives the ultrasonic pulses that are emitted by the receiver 5 in one direction but are reflected to return in a reverse direction.

Figure 2:
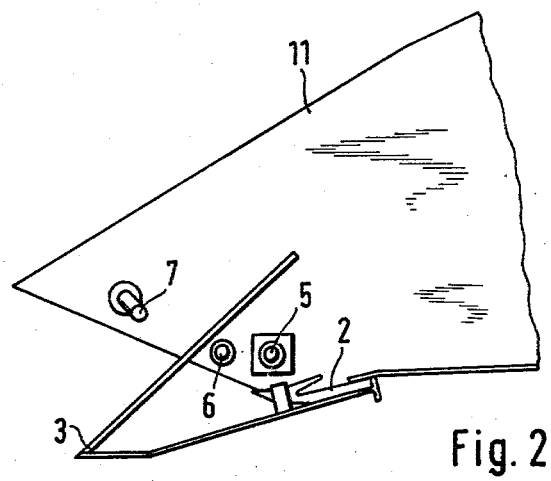
FIG. 2 shows a sectional side view of the embodiment of FIG. 1.

As shown in FIG. 2, the reflection receiver 6 can be positioned at the same level as, and very close to, the receiver-transmitter 5. Such a positioning allows the registration of growth that is already aligned by the stalk lifters 3 because the receiver 5 and the reflection receiver 6 are located below the plane of alignment set up by all of the stalk lifters 3.

The directional microphone 7, on the other hand, is located above the alignment plane set up by the stalk lifters 3. The use of the reflection receiver 6 and of the directional microphone 7 makes possible a sufficiently precise density measurement of the vegetation even in cases of a deeply bent or lying crop. In addition, it is advantageous to employ stalk lifters which are larger than usual stalk lifters and which are set relatively close together on the cutter bar, since the lifters are intended not only to align the stalks and guide them to the cutting knives in the usual manner, but also to hold the stalks sufficiently high to allow the ultrasonic field to penetrate the vegetation with a minimum of interference.

Figure 3:
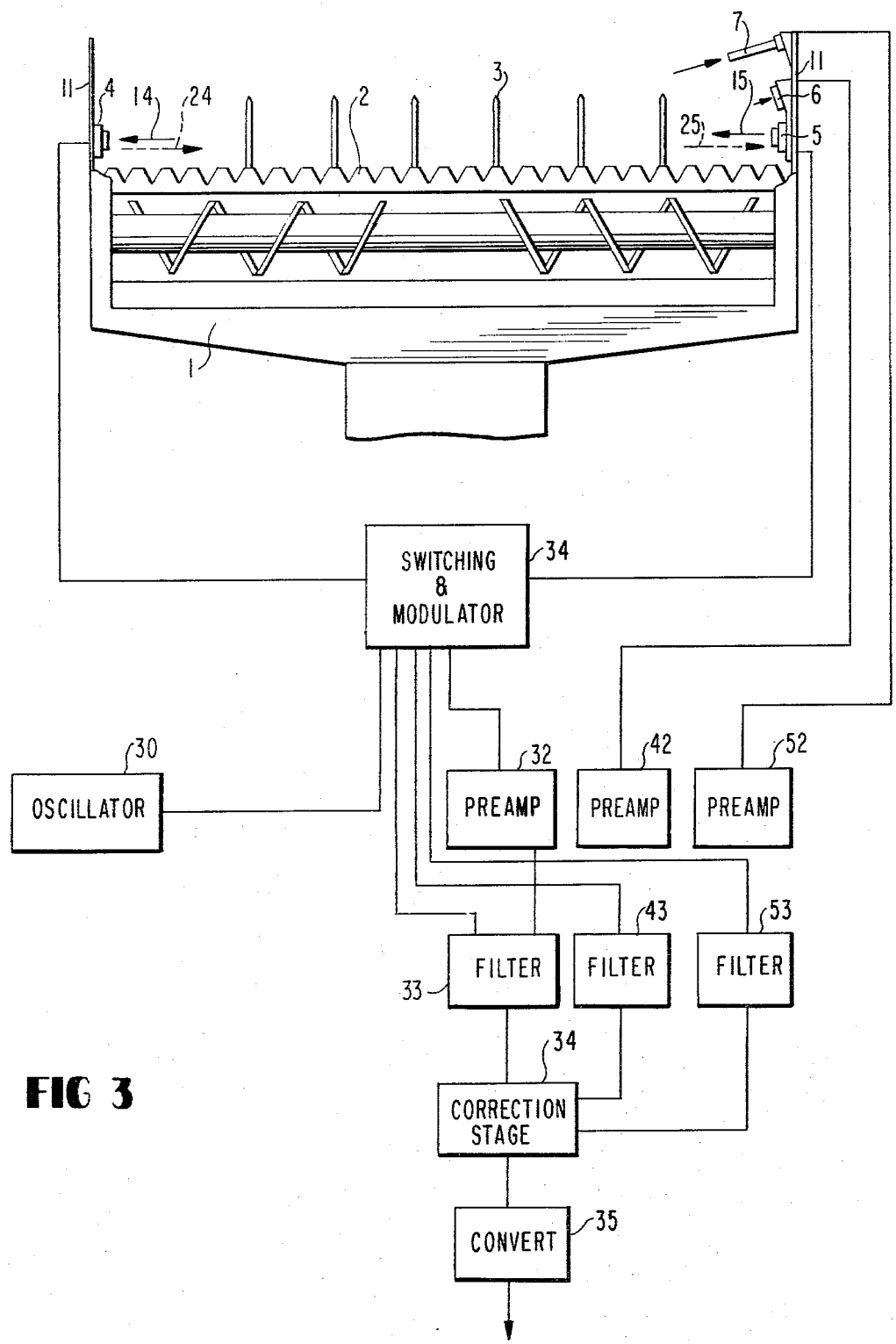
FIG. 3 shows a top view of the embodiment of FIG. 1 in combination with a block diagram of an associated embodiment for signal processing and correction.

The processing of the ultrasonic pulses or signals and their possible correction will now be discussed with reference to FIG. 3. An oscillator 30 produces an alternating voltage having the desired ultrasonic frequency, for example of a magnitude of 4000 cps. This alternating voltage should be kept at a constant value and its frequency should be stabilized. The alternating voltage is applied to a switching and modulator unit 31 that chops the alternating voltage into adjustable clock pulses having a particular frequency and pulse width, for example 100 clock pulses per second with a pulse width of 4 milliseconds. The chopping is accomplished by the modulator section of the switching and modulator unit 31.

The switching section feeds the ultrasonic clock pulses into one of the acoustic transducers, the transmitter-receiver 4 or the transmitter-receiver 5, a feeding which additionally can also take place in an alternate sequence. The signals arriving at the receiver 4 or 5 are then transmitted again by way of the switching and modulator unit 31, to a preamplifier 32. The switching and modulator unit 31 not only switches the transmitter-receivers 4 and 5 in a predetermined sequence into the transmitting mode but also switches in the appropriate manner the non-transmitting acoustic transducer to the receiving mode, with the possibility of taking into consideration the ultrasonic transit time from transmitter to receiver when determining the time of reception.

The pre-amplifier 32 amplifies the signals being received and also removes to some extent interfering signals and pulses. A filter stage 33 is connected in series with the pre-amplifier 32 for comparing the precise signal frequency as well as matching the transit times of the transmitter frequencies which are received directly with those that, due to reflection, arrive at the receiver with a time lag. For this reason, the filter stage 33 is also connected with the transmitter, output side of the switching and modulator unit 31.

The filter stage 33 may also be equipped with an interference blanking device for eliminating the cyclic portion of parasitic noise signals, for example typical knife-generated noises, which arrive during intervals without transmitter signals. In operation, the blanking device acts to superimpose the parasitic noise signal of opposite sign on the received acoustic pulse signal, thus eliminating the cyclic portion of the interfering noise signal. The interfering noise signal may originate at the transducer 4, 5 previously operating as a transmitter, as well as at an additional microphone, such as the microphone 6.

A signal is formed at the output of the filter stage 33 which is proportional to the difference between the emitted ultrasonic beam 24 and each ultrasonic beam 25 that is received. The signal obtained as the result of the ultrasonic absorption measurement is insufficient by itself to characterize the typical features and the density of the vegetation. For this reason, the additional signals obtained from the reflection measurements are also used.

As mentioned above, one portion of the ultrasonic pulse reflections is picked up by the additional microphone 6 and the corresponding reflection signals are fed into a preamplifier 42, where the signals are amplified and roughly filtered. A more exact filtering and a blanking of interferences is accomplished for these signals in a filter stage 43 which is connected in series with the pre-amplifier 42.

The deflected signals from the depth of the vegetation which are picked up by the above-mentioned directional microphone 7, are processed in the same manner. The pre-amplification and rough filtering is accomplished in this case by the preamplifier 52 and the exact filtering and interference blanking is performed by the filter stage 53. It is advantageous to align the transit time of the signals that are picked up by the directional microphone 7 to make possible their evaluation with respect to the signals that are received by the receiver 5.

The processed absorption signals of the filter stage 33 and the reflection signals from the filter stages 43 and 53 are then combined in a correction stage 34. Important in this connection is the possibility of deriving, from the absorption and reflection ratio, an estimate of the moisture of the material, the presence of other vegetation and other features characterizing the density of the material to be harvested.

From a properly and selectively chosen mixture of the signal portions, there is thus obtained in the correction stage 34 a signal that corresponds to and identifies the features that influence the processing of the material being harvested, including the influence of brush wood, the moisture content of the material and the like. Such a signal is functionally related not only to the loss of intensity of the signals across the ultrasonic transmitter and receiver but also to the transit time, and in certain cases to the phase shift, between the transmitter and receiver. The signal from the stage 34 is then corrected in a converter 35 in conformity with the exponential relation between density and absorption variations, with the desired control signal appearing and obtainable at its output.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. In a harvest machine of a type having harvesting tools at the front end thereof for cutting plant growth as the harvest machine moves forward, the harvesting tools emitting ultrasonic noise signals, the improvement of noise insensitive apparatus for measuring the density of plant growth in a cutting area in front of said harvesting tools and for controlling the forward movement of the harvest machine is response to the measured density, the apparatus comprising:

transmitter means for transmitting an intermittent beam of frequency modulated ultrasonic pulses through said cutting area in a direction transverse to the forward direction of travel of said harvest machine, the transmitted ultrasonic pulses being deflected and absorbed by plant growth in said cutting area;

absorption receiver means disposed opposite said transmitter means and operable to receive signals for a particular period following an acoustic time delay after each of said ultrasonic pulses is transmitted, the acoustic time delay and particular period defined to allow said receiver to receive the ultrasonic signal pulses of said transmitter means that pass through the plant growth in the cutting area;

means for subtracting the noise signals generated during each particular period from the signals received by said receiver means during the particular period;

reflection receiver means disposed forwardly and in a lateral spaced relation with respect to said absorption receiver means for receiving the ultrasonic pulses of said transmitter means that are reflected by the plant growth in said cutting area out of a transverse line between the transmitter means and the absorption receiver means; and means for evaluating the intensity, time delay and/or phase position of the ultrasonic pulses received by said absorption receiver means and said reflection receiver means to generate a harvest machine control signal for controlling the forward movement of the harvest machine.

2. The apparatus of claim 1 wherein said means for subtracting includes means for detecting interfering noise signals in said cutting area and subtracting the detected interfering noise signals from the signals received at said absorption receiver means to eliminate the interfering noise signals from the frequency modulated ultrasonic pulses of said transmitter means that are received at the absorption receiver means.

3. The apparatus of claim 1 including means for reversing the functions of said transmitter means and said absorption receiver means to continuously alter the direction of transmission of said ultrasonic pulses.

4. The apparatus of claim 1 including echo receiver means disposed adjacent said transmitter means for receiving the transmitted ultrasonic pulses of the transmitter means that are reflected back from the cutting area.

5. The apparatus of claim 1 wherein said transmitter means includes means for simultaneously transmitting two ultrasonic pulses of different frequency and said means for evaluating includes means for evaluating the intensity, time delay and/or phase position of at least one of the two transmitted pulses to generate a harvest machine control signal for controlling the forward movement of the harvest machine.

6. The apparatus of claim 1 wherein said harvesting tools include spaced cutting jaws and a reaper beam and stalk lifters arranged between the cutting jaws and said transmitting means, absorption receiver means and said reflection receiver means are positioned transversely, forward of the reaper beam on the cutting jaws.

7. The apparatus of claim 6 wherein said transmitting means and said absorption receiver means are positioned transversely rearward of front ends of said stalk lifters.

8. The apparatus of claim 7 wherein said reflection receiver means is situated transversely rearward of the front ends of the stalk lifters.

9. The apparatus of claim 8 including two additional receiving means for receiving the transmitted ultrasonic pulses, one of the additional receiving means being positioned above the plane of the stalk lifters and the other of the additional receiving means being positioned below the plane of the stalk lifters.

* * * * *